United States Patent
Bechmann et al.

(10) Patent No.: US 6,508,604 B1
(45) Date of Patent: Jan. 21, 2003

(54) ARTICLE COMPRISING A CELL SYSTEM

(75) Inventors: Georg Rudolf Theobald Bechmann, Wezembeek-Oppem (BE); Joseph Fernand Deflander, Wespelaar (BE); Neil John Rogers, Brussels (BE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/936,407

(22) PCT Filed: Mar. 17, 2000

(86) PCT No.: PCT/US00/06986

§ 371 (c)(1),
(2), (4) Date: Sep. 11, 2001

(87) PCT Pub. No.: WO00/56627

PCT Pub. Date: Sep. 28, 2000

(30) Foreign Application Priority Data

Mar. 19, 1999 (EP) .............................. 99870053

(51) Int. Cl.[7] .................. A45D 34/04; A45D 37/00
(52) U.S. Cl. .................. 401/132; 222/541.3; 401/133; 604/3
(58) Field of Search ................. 401/132–135; 222/541.1, 541.3; 604/3

(56) References Cited

U.S. PATENT DOCUMENTS

| | | | |
|---|---|---|---|
| 1,221,227 A | 4/1917 | Schulz |
| 1,309,201 A | 7/1919 | Hollister |
| 2,961,677 A | 11/1960 | Zecchini |
| 3,016,308 A | 1/1962 | Macaulay |
| 3,295,537 A | 1/1967 | Young, Jr. |
| 3,334,374 A | 8/1967 | Watkins, Jr. |
| 3,451,758 A | 6/1969 | McClain |
| 3,503,783 A | 3/1970 | Evans |
| 3,519,364 A | 7/1970 | Truhan |
| 3,576,987 A | 5/1971 | Voight et al. |
| 3,757,782 A | 9/1973 | Aiken |
| 3,759,389 A | 9/1973 | Firth |
| 3,768,916 A | 10/1973 | Avery |
| 3,810,841 A | 5/1974 | Richter |
| 3,826,259 A | 7/1974 | Bailey |
| 3,871,357 A | 3/1975 | Grosso et al. |
| 3,874,504 A | 4/1975 | Verakas |

(List continued on next page.)

FOREIGN PATENT DOCUMENTS

| | | |
|---|---|---|
| BE | 855362 | 3/1977 |
| DE | 2549065 | 5/1977 |
| DE | 3545926 C2 | 3/1989 |
| EP | 0046021 B1 | 2/1985 |
| EP | 0066463 B1 | 7/1985 |
| EP | 0188883 A2 | 7/1986 |
| EP | 0290310 A1 | 11/1988 |
| EP | 0340993 A2 | 11/1989 |
| EP | 0280784 B1 | 11/1990 |
| EP | 0404500 A2 | 12/1990 |
| EP | 0271976 B1 | 2/1991 |
| EP | 0442659 A1 | 8/1991 |
| EP | 0495743 A1 | 7/1992 |
| EP | 0291284 B1 | 9/1992 |

(List continued on next page.)

Primary Examiner—Timothy L. Maust
Assistant Examiner—Kathleen J. Prunner
(74) Attorney, Agent, or Firm—Peter D. Meyer

(57) ABSTRACT

A cell system has one or multiple burstable enclosures or closed cells which contain an active composition, such as a fluid or solid (including powdered) product, preferably a liquid product, which is released therefrom when the enclosures or closed cells are ruptured. Each enclosure or cell is provided with a flow control which controls the direction and flow of the composition outwardly of the enclosure or cell when the enclosure or cell is ruptured. The flow control is formed by a film covering one side of an enclosure or cell with the film having a cut-out portion forming a flow control window. The composition can be a face cleaning lotion or cream, a disinfectant, a household cleaning composition, a perfume, a polish or a medicament.

12 Claims, 3 Drawing Sheets

U.S. PATENT DOCUMENTS

| | | |
|---|---|---|
| 3,929,135 A | 12/1975 | Thompson |
| 4,081,256 A | 3/1978 | Donnelly |
| 4,140,409 A | 2/1979 | DeVries |
| 4,216,104 A | 8/1980 | Gergely |
| 4,236,652 A | 12/1980 | Beguhn |
| 4,259,383 A | 3/1981 | Eggensperger et al. |
| 4,291,697 A | 9/1981 | Georgevich |
| 4,324,246 A | 4/1982 | Mullane et al. |
| 4,331,264 A | 5/1982 | Staar |
| 4,342,314 A | 8/1982 | Radel et al. |
| 4,415,288 A | 11/1983 | Gordon et al. |
| 4,430,013 A | 2/1984 | Kaufman |
| 4,462,224 A | 7/1984 | Dunshee et al. |
| 4,674,237 A | 6/1987 | Sullivan |
| 4,878,775 A | 11/1989 | Norbury et al. |
| 5,090,832 A | 2/1992 | Rivera et al. |
| 5,120,301 A | 6/1992 | Wu |
| 5,158,349 A | 10/1992 | Holland et al. |
| 5,456,704 A | 10/1995 | Kilcullen |
| 5,560,922 A | 10/1996 | Chien et al. |
| 5,658,084 A | 8/1997 | Wirt |
| 5,674,270 A | 10/1997 | Viltro et al. |
| 5,704,723 A | 1/1998 | Salisian |
| 5,804,300 A | 9/1998 | Maro et al. |
| 6,284,396 B1 | 9/2001 | Kaule et al. |

FOREIGN PATENT DOCUMENTS

| | | |
|---|---|---|
| EP | 0161091 B1 | 5/1993 |
| EP | 0540184 A1 | 5/1993 |
| EP | 0543406 A1 | 5/1993 |
| EP | 0294189 B1 | 8/1994 |
| FR | 1118205 | 6/1956 |
| FR | 2632936 | 12/1989 |
| FR | 2653059 | 4/1991 |
| FR | 2754744 | 4/1998 |
| GB | 1328641 | 8/1973 |
| GB | 2289411 A | 11/1995 |
| WO | WO 89/10156 A1 | 11/1989 |
| WO | WO 93/10019 A1 | 5/1993 |
| WO | WO 94/03369 A1 | 2/1994 |
| WO | WO 94/09735 A1 | 5/1994 |
| WO | WO 94/12088 A1 | 6/1994 |
| WO | WO 94/14356 A1 | 7/1994 |
| WO | WO 96/23700 A1 | 8/1996 |
| WO | WO 96/28262 A1 | 9/1996 |
| WO | WO 97/04831 A1 | 2/1997 |
| WO | WO 97/34816 A1 | 9/1997 |
| WO | WO 98/17263 A1 | 4/1998 |
| WO | WO 00/56626 A1 | 9/2000 |

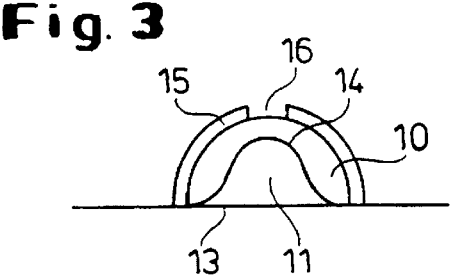
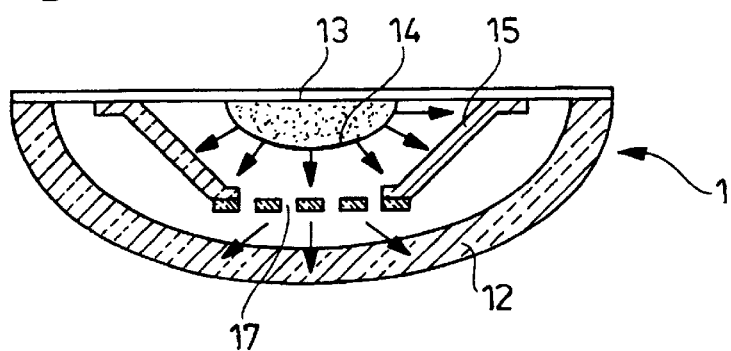
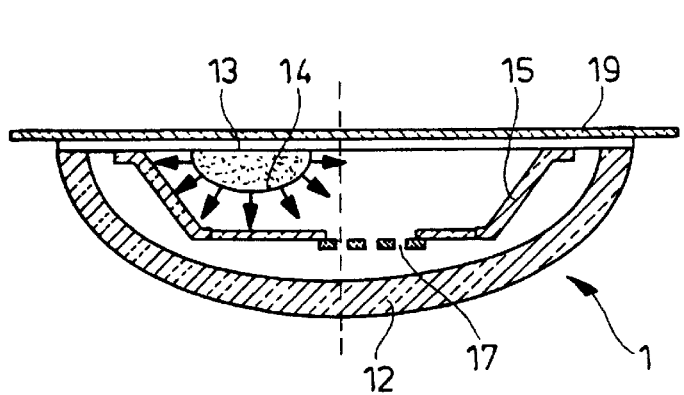
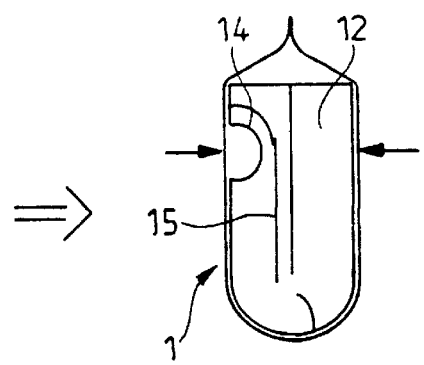

ARTICLE COMPRISING A CELL SYSTEM

FIELD OF THE INVENTION

The present invention relates to articles comprising a cell system with at least one cell filled with an active composition, the cell system further comprising a means for controlling the direction and flow of the cell's contents, once said at least one cell has been ruptured.

BACKGROUND OF THE INVENTION

Disposable articles comprising at least one capsule filled with an active composition associated to a substrate, for example a cotton pad are representative of the various articles to which the present invention can apply; such disposable articles typically comprise at least one capsule filled with an active composition, at least one element made out of an absorbent material. At the time the user breaks the capsules, their contents spreads onto the absorbent material and the disposable article is ready to use.

The following references are directed to such articles comprising a capsule system associated to an absorbent substrate: U.S. Pat. No. 4,878,775 (D1) is a U.S. patent to 3M. It discloses a device comprising burstable microcapsules containing a liquid, at least one sheet of a carrying substrate, and at least one sheet of a flexible liquid permeable material overlaying the microcapsules. Pressure on the device breaks the microcapsules and the liquid is dispensed on/through the liquid permeable sheet. U.S. Pat. No. 3,768,916 (D2) is a U.S. patent to Medical Supply C$^y$. It discloses a sponge comprising a hollow portion into which a glass ampoule is inserted. When the ampoule is broken by the user, the contained disinfectant soap impregnates the sponge for wound-cleaning use. U.S. Pat. No. 5,090,832 (D3) is a US patent to Colgate It discloses a disposable pad comprising a scrubber layer, a blotter layer of absorptive material and a liquid impervious sheet located between the scrubber and the blotter layers. The pad further comprises at least one packet containing sufficient cleaning material to saturate the scrubber layer when ruptured. FR 2,754,744 (D4) is a French patent application to A, Soares Duarte. It discloses a flexible film comprising cells filled with liquid. The cells are ruptured when pressure is exerted and the contained liquid is released and impregnates a support. DE 3,545,926 A1 (D5) is a German application to A. G. Frühauf. It discloses a system in which the capsules are made out of a material which does not rupture, but in which the seals between the two constitutive layers of said capsules are delaminated under pressure. Then, the cell contents is free to flow between said layers up to punctured holes through which it is dispensed. EP 0 294 189 A2 (D6) is a German patent application to Jaypak Ltd. It discloses a flexible bag combined to an absorbent applicator. The bag is burst to release the liquid inside the applicator.

None of the above documents D1 to D4 and D6 raises nor solves the problem of controlling the flow and direction of the cell's contents to the outside medium, once the cell has been ruptured.

D5 discloses a cell system wherein the cells are not ruptured, but their constitutive layers are delaminated when the user exerts a pressure on the cell. The contents is then directed through channels created between the delaminated layers, up to holes punctured in one layer, through which it can escape to the outside. One disadvantage is: the way the layers delaminate is not predictable, and thus the direction of the contents is not predictable. Moreover, depending on the surface of delaminated film, the number of punctured holes which is accessible to the flowing contents can vary, is not predictable, and cannot be controlled.

It is therefore one main object of the present invention to provide the user with an article comprising a cell system with at least one cell filled with an active composition, the article further comprising a means for controlling the flow and direction of the cell's contents, once said at least one cell has been ruptured.

SUMMARY OF THE INVENTION

The present invention is directed to a cell system with at least one burstable cell filled with an active composition, the cell system being characterized in that it comprises a means to control the flow and direction of the cell's contents, once said at least one cell has been ruptured. More generally, the present invention is directed to an article which comprises such a cell system. Preferably, the cell system is associated with a dispersing element, such as for example a fibrous pad. Preferably, the force required to burst the cells is comprised within the range of 10 to 80 N. More preferably, the article is constructed so that less than 10% product is lost per year at 35° C./20%RH, the barrier properties being achieved by selecting a barrier material for making either the cells, or an openable outer package hermetically closed around at least one article.

BRIEF DESCRIPTION OF THE DRAWINGS

The invention will now be explained in detail with reference to the accompanying drawings, in which:

FIG. 3 is a profile cut view showing one cell, with screen window to control the direction and flow of the cell's contents, once the cell has been burst.

FIG. 4 is a profile cut view of an article according to one embodiment of the present invention, the article comprising a cell system, a flow-control means, and an absorbent support, the cell being centered relatively to the window of the flow-control means.

FIG. 5a is a profile cut view of an article according to one embodiment of the present invention, the article comprising a cell system, a flow-control means, and an absorbent support, the cell being off-centered relatively to the window of the flow-control means.

FIG. 5b is similar to 5a, but the article is shown in folded configuration, as it is packed prior to its use.

DETAILED DESCRIPTION OF THE INVENTION

Figure 1:
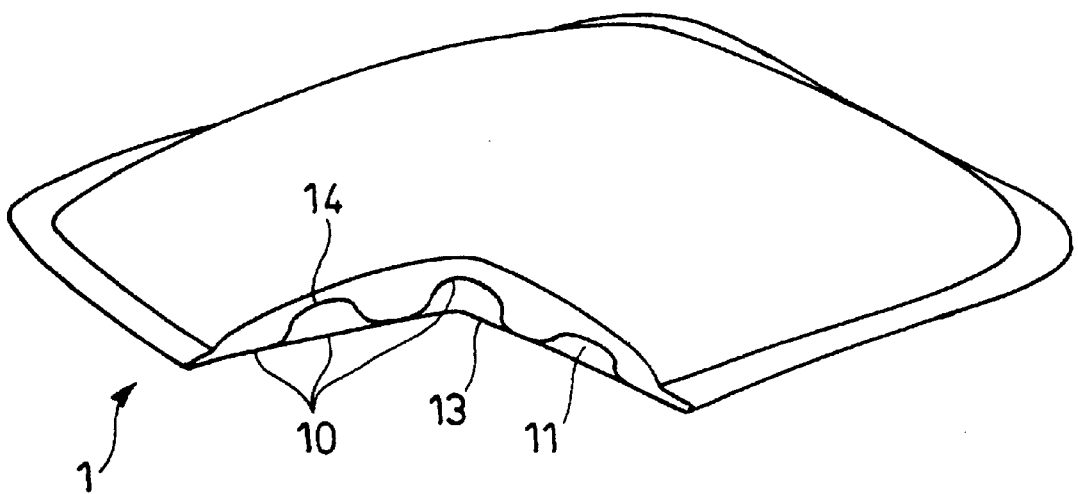
FIG. 1 is a perspective view of an article according to the present invention, comprising a cell system and a flat absorbent support.

The present invention is related to a cell system which has one or multiple enclosures or closed cells which contain fluid or solid (including powdered) products, preferably liquid products, which are released from the individually sealed enclosures for example via the increase of internal pressure within the enclosure eventually leading to rupture of one of the enclosing materials or a seal that may be present between two pieces of enclosing material. As alternatives to compression, a gas-producing reaction can be initiated to increase the cell's internal pressure to the point of rupture, or the cells can be dissolved by using a chemical reaction between the material of the cell's walls and an external reactant.

The invention is more generally related to an article comprising a cell system with at least one burstable cell filled with an active composition. The cells are ruptured by one means or another thus opening the chambers to exposure to: (i) the outside environment; (ii) an internal constrained (but larger volume) environment within the system or article; or, (iii) other fluids (e.g., gases) outside of the original chambers which may enter into the previously sealed chambers. The purpose of such exposure is to provide a useful benefit to the user including but not limited to: dispensing fluids or solids (including powders) in the cells to contact and optionally disperse onto a target surface for a variety of purposes; mixing different materials from different cells to cause a useful chemical reaction as described above; exposing a reactive material to a fluid (e.g., gaseous air or liquid water) found in the environment to cause a useful chemical reaction where either the chemical composition or even the phase state of the end products of the reaction or the energy/heat flow of the reaction may be the useful endpoint sought; exposing a fluid or solid to the gaseous environment for the purpose of volatilizing and distributing components of said fluids or solids.

The above-mentioned applications for the present invention can be directed to a multitude of user-beneficial outcomes including, but not limited to: cleaning and/or rubbing, bleaching, cooling, heating, deodorizing, disinfecting, medicating, wiping . . .

The article of this invention optionally but preferably features a support absorbent material designed to absorb the product upon release. This support material is designed to assist the user in the application of the product.

For the article, barrier properties are required to prevent significant product(s) loss through permeation (i.e. less than 10% product loss/year at 35° C./20%RH and the product(s) must keep the activity it is designed for). The barrier properties are provided by a high barrier material, which can be either the material for making the cells, or the material for making a secondary package, as further explained hereafter. Furthermore, it has been found that most of such barrier materials are difficult to rupture, and thus, in case said barrier material is used for making the cells, an easy opening means is preferably added to said cells to facilitate their rupture by the user.

The cells

As shown in FIGS. 1 to 10, the article (1) is provided with a cell system (10) which comprises at least one cell (11) filled with an active composition, which can be either solid, particles, granulates, powder, liquid, or even a gas, but is preferably a liquid composition. Depending on the purposes, the cell system (10) can comprise two or more cells, filled with the same, or different compositions (see example of contained compositions below). The cell system (10) can be used by itself, or it can also be coupled to a solid medium, for example an absorbent support (12). It can also be integrated into a pouch filled with liquid or gas.

One cell (11) comprises a bottom (13) and a dome (14). The dome (14) can be made out of a flat film which is deformed into the cavities of a mold, for example by a thermoforming process, or vertical (VFFS) or horizontal (HFFS) form fill and seal process in the case the cells have the shape of a sachet (see description hereafter). Once filled with the active composition, the dome (14) is closed by sealing the bottom (13) which preferably is a flat film. The cells (11) are ruptured by applying a constraint onto their surface which can be mechanical such as a pressure, a tearing or peeling movement; or a chemical or hydration reaction which dissolves the surface of the cell. In one embodiment, the cells (11) are burst when the user applies a compression force on the top or the sides of the cell, as shown for example in FIG. 6c. This leads to rupture one portion of the dome (14) of the cell (11). The cell (11) normally ruptures in its dome portion (14). This is due either to the fact that the material used to make the cell bottom is chosen as more resistant to rupture than the material for the dome (14), or in case the same materials are used for forming the bottom (13) and the dome (14), this is due to the manufacturing process: since the dome (14) is thermoformed in this example, its constitutive material thins down in at least one point, where mechanical properties, and especially resistance to burst, are decreased. In another embodiment, the cells (14) are chemically dissolved. In another embodiment, rupture of the cell is achieved by an easy opening means, as will be further described hereafter.

The cells (11) can have any shapes or dimensions, such as for example parallelepipedic, oval or hemispheric, but while not being limited, their internal volume is preferably comprised within the range of 0.01 to 5.0 ml, more preferably within the range of 0.4 to 2.0 ml. For example in the case the cells are substantially hemispheric, their diameter is preferably comprised within the range of 10 to 20 mm and their depth is between 6 and 15 mm. Preferably, 50 to 99% of one cell's volume is filled with liquid. In the case of cells filled with a liquid active composition, the cell (11) is made out of a liquid impervious material.

While the cell bottom and top can be joined or sealed by a variety of known techniques including adhesives, the cell's material should preferably feature good sealing properties and mechanical properties such that the user can rupture the cells to get the contained active composition out by applying a reasonable force, while the cells need to be strong enough not to rupture prematurely, for example during manufacturing, storage or transportation. Furthermore, the material shall be chosen such that it does not produce sharp particles once broken, especially glass shall not be used since it produces glass splinters which can be very dangerous for example when the article (1) is used for facial/body cleaning purposes.

Figure 6:
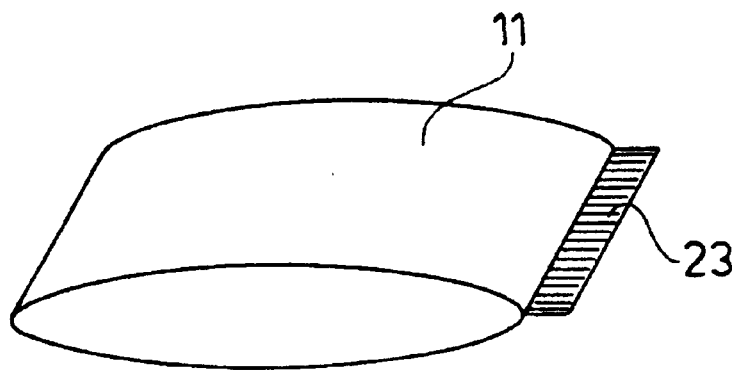
FIG. 6 is a profile schematic view showing one cell of the cell system formed as a sachet.

In another embodiment, the cells (11) have the shape of sachets, as shown for example in FIG. 6. Such sachets (11) are made out of a film which is folded and sealed. Preferably, the sachet also comprises an easy opening means, more preferably it comprises at least one peelable seal (23) which ruptures when the user applies sufficient pressure on the sachet.

Typically, the force to be applied by the user to rupture one cell, is substantially comprised within the range of 10 to 80 N (force applied on top of the cell). Preferably, the force to be applied to burst the cells (11) is less than 60 N, more preferably less than 40 N. Most preferably it is comprised within the range of 10 to 20 N. It has been found that this force to burst usually decreases for a same cell when the force is applied on the sides for substantially hemispheric shaped cells.

In one first embodiment of this invention, the material for making the cells is defined as a barrier material. Such a material is defined as having a permeation of less than 10% product loss/year at 35° C./20%RH, so that the active composition keeps the activity it has been designed for. Typically, such properties are achieved by using a film which is: liquid impervious in that no liquid passes through it after 30 sec.; a barrier to vapors/solvents in that its water vapor transmission rate (WVTR) is less than 6 g/sqm/day at 40° C./90%RH; and optionally a barrier to gases, in that its $O_2$TR (oxygen transmission rate) is less than 200 cc/sqm/day/atm at 23° C./50%RH.

The barrier film can have one thick layer of a thermoplastic, but is preferably a laminate material comprising at least one layer of a barrier material such as an aluminium laminate for example, which is sandwiched between thermoplastic outer layers, for good sealing properties of the film. In a most preferred embodiment, the film is laminated comprising at least one aluminium layer which gives very good barrier properties to liquids, gas and vapors, for example a LDPE/Alu/PET having a thickness of respectively 80 µm/9 µm/12 µm. Such a laminate comprising a layer of metal between layers of polyolefins for sealing properties is preferably to be used in case the cells have the shape of sachets. Other options can be to use thick thermoplastics, such as high density polyethylene (HDPE) more than 50 µm thick, or polypropylene (PP) more than 100 µm thick, or low density polyethylene (LDPE) more than 150 µm thick. Despite such materials are not specifically high barrier materials, the thickness which is used is such that it allows good barrier properties of the cells.

The thickness of the material used for making the cells should be adapted to the nature of the material which is used, so that said thickness is as little as possible while keeping barrier properties as defined above. It is preferably comprised within the range of 35 to 90 µm, more preferably within the range of 35 to 50 µm. When the thickness is below 35 µm, it was found that manufacturing problems appear, for example wrinkles appear during thermoforming, and the force to rupture the cells is decreased—typically below 10 N—which leads to premature burst. Thicknesses above 90 µm may be used, such values will however lead to cells which are particularly resistant to rupture.

It has been found that when cells are constructed with materials having barrier properties as defined above, the force to burst is often more than the acceptable value (i.e. 10 to 80 N). This is due firstly to the thickness of the film which is limited to a minimal value, under which the barrier properties are not achieved, and/or secondly to the nature of the polymer. This is why optionally but preferably, each cell of the cell system according to this embodiment of the invention is provided with an easy opening means. Several possible embodiments of easy opening means can be applied to the present invention, which are discussed hereafter.

In a second alternative embodiment of the invention, the cells are made out of a material which is non barrier. The material is preferably a thermoplastic, such as polypropylene or polyethylene. More preferably, said material is a low density polyethylene film (LDPE film) which features good processability, especially when using a thermoforming process. In any case, it has been found that acceptable rupture properties for the capsule are achieved for a film with limited thickness—typically less than 90 µm. This however leads to low barrier properties: in particular when one of the water vapor transmission rate (WVTR) is higher than 6 g/sqm/day at 40° C./90%RH, and optionally the $O_2$TR (oxygen transmission rate) is higher than 200 cc/sqm/day/atm at 23° C./50%RH, at least some ingredients of some composition can escape from the capsule thus leading to a change in the proportions of the composition, and modification of its properties. It has further been found that such changes are rapid enough to appear during the period of time between the manufacture of the capsule system, and its use (including transportation and storage periods). In the present alternative embodiment, due to the poor barrier properties of the cell's walls, a separate secondary package is provided which is made out of a barrier material. Such secondary barrier packages are hereafter described in detail.

The easy-opening means

In the case the cells are made out of a barrier material, the force to burst the cell can be more than an acceptable value for the user—typically more than 80 N—, and so the cells (11) are provided with an easy opening means.

In one first embodiment, said easy opening means is achieved by applying a laser scoring onto the surface of the cell. Preferably, said laser scoring is located on the cell's dome, more preferably on the top portion of said cell's dome. Techniques for making such laser scorings are well known in the art. The shape and dimensions of the laser scoring may be determined by those skilled in the art, such as to create a cell which can be burst when applying a force comprised within the range of 10 to 80 N, preferably, 10 to 60 N, more preferably 10 to 40 N, and most preferably within the range of 10 to 20 N. The advantage of such an easy opening means is that it decreases the force to burst the cell, by creating an area in its walls where the thickness is decreased. However, the barrier properties are only marginally affected by the lower thickness, since the surface of the laser scoring is very limited.

In a second embodiment of the present invention, the easy opening means is achieved by providing the cell with at least one elongated portion. Such an elongated region has a lower thickness compared to the rest of the cell's walls. The optimum thickness for the elongated portion may be determined via a sampling/trials procedure, and will typically depend on the nature of the material, nature of the contents, temperature of use, so as to achieve barrier properties as defined above. In any case, the volume inside said elongated portion should preferably be less than 10% of the cell's total volume, more preferably less than 5% of the cell's total volume, and most preferably less than 2% of the cell's total volume. In this way, the exchanges of gases, vapors, and solvents, as well as the risk of leaking (in case the cell's contents is a liquid) are limited over the period from the manufacture to the use. Alternatively but similarly, the easy opening means is an elongated portion of the cell, with less thickness, but which is inverted, so that it is pointing in the inside of the cell. At the time the user presses onto the cell, the inverted protrusion comes inside out and bursts to release the cells contents.

Figure 7:
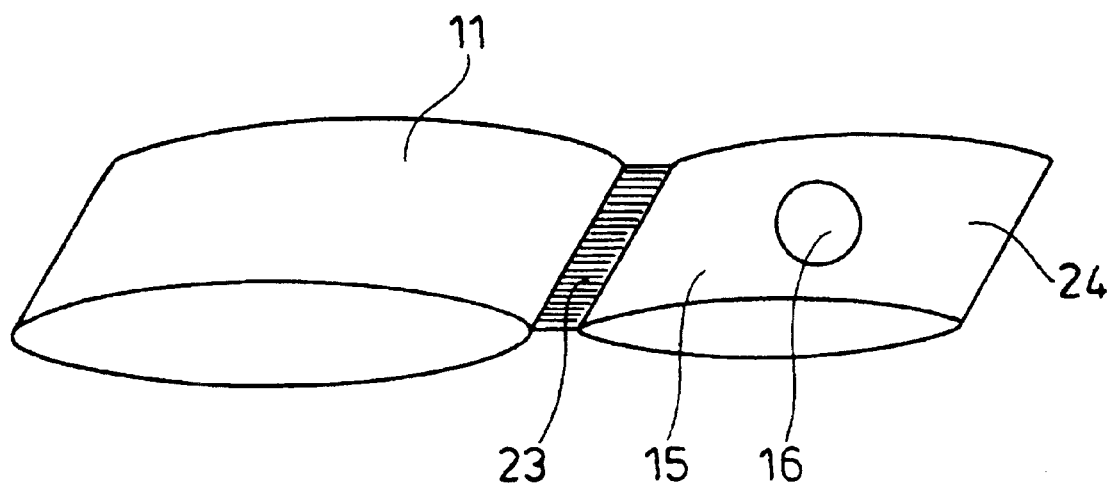
FIG. 7 is a profile schematic view showing one cell of the cell system with integral flow-control means.

In a third embodiment of the present invention, the easy opening means is achieved by a peeling area located at the interface between the dome of the cell and its bottom part. When the user presses on the top of the cell, an internal pressure is created inside the cell, which peels the seal off. Techniques of making seals between two films are well known in the art, and a skilled person will easily find the correct parameters when making the seal, so that the force to peel off the seal is preferably comprised within the range of 10 to 80 N, as previously described. Such techniques include heat sealing, hot gluing, cold gluing which are well known techniques in the field of making seals. Alternatively, when the cell has the shape of a sachet made by a VFFS or HFFS forming process, the peeling area can be a weak seal (23), as shown in FIG. 7 for example. In one embodiment, the weak seal (23) is located on a side of the sachet. In another embodiment, the sachet (11) comprises at least two compartments separated by a weak seal (23), the first compartment being closed and filled with a composition, and the other compartment being punched with a cut-out portion (16). When the user presses on the first closed compartment, the median weak seal (23) breaks and the composition passes to the second compartment, and is dispensed through the cut-out portion which acts as a means for controlling the direction and flow of released composition.

In a forth embodiment of this invention, the easy opening means is achieved by an O-ring shaped cell. The cell's contents is located inside circular peripheral walls. The cell further comprises a central channel. The outer seal is strong while the inner seal is weak. When pressure is applied onto the cell, the central weak seal breaks, and the cell's contents is released to the outside through the central channel of the cell. This further allows to control the direction of the released contents.

In a fifth embodiment of the present invention, the easy opening means is achieved by a pull string which is attached to at least one portion of the cell. The pull string comprises an attachment portion, which is fixed to the cell, and a free portion which is long enough to be reached and pulled by the user. Usually, cells are ruptured by pressing onto them, in this case the user's force is dispersed over the surface of contact comprised between the fingers and the cell. When the cell's material is difficult to rupture, the force needs to be more concentrated to one point of the cell, to be more effective in rupturing said cell. Such a concentration is achieved by using the pull string having a small diameter (preferably less than 1 mm), which is fixed to a limited surface of the cell. For example, it can be attached all around the periphery of the cell. It can also be attached around a portion liking two cells. It can also be attached to certain points of the periphery of the cell, at the seal region between the dome and the bottom of said cell. The pull string can be attached directly to the bottom of the cell, thus passing through the cell. It can also be attached to the top part of the cell's dome.

In a sixth embodiment of the present invention, the easy opening means is providing each cell of the cell system with at least one peelable seal, said at least one peelable seal further comprising a pull string. The user releases the cell's contents by pulling on the pull-string, thus peeling off the weak seal. Preferably, said peelable weak seal is a portion located at the interface between the dome and the bottom of the cell.

The two preceding embodiments are also applicable in the case the cell has the shape of a sachet made by a VFFS or a HFFS forming process.

The outer package

In the case the cells are made out of a material which is not a barrier to the cell's contents, an outer package is provided which can be of any type suitable for containing at least one disposable article (1). Said outer package can be a separate element, for example a wrap-around film which surrounds at least one disposable article (1), a laminated carton, a glass or plastic jar. Alternatively, it is an outer package element (19) integrated to the disposable article (1) itself, as shown for example in FIG. 5a. As explained above, the material used for the cell (11) is chosen such that the cell (11) shows a low burst force but this leads to poor barrier properties, and thus modifications of the contained active composition by permeation of some components of the composition through the cell (11). Said outer package is defined as being made out of a barrier material. Such a material is defined as follows for a thickness of 25 $\mu$m: it is liquid impervious in that no liquid passes through it after 30 sec.; it is a barrier to vapors/solvents in that its water vapor transmission rate (WVTR) is less than 6 g/sqm/day at 40° C./90%RH; also optionally, it is a barrier to gases in that its $O_2$TR (oxygen transmission rate) is less than 200 cc/sqm/day/atm at 23° C./50%RH.

In one embodiment, the outer package is a film which is folded and sealed around at least one article (1), for example by using a wrap-around or wrapping process. The film can have one thick layer of a thermoplastic, but is preferably a laminate material comprising at least one layer of a barrier material such as an aluminium laminate for example, which is sandwiched between thermoplastic outer layers, for good sealing properties of the film. In a most preferred embodiment, the film is laminated comprising at least one aluminium layer which gives very good barrier properties to liquids, gas and vapors, for example a LDPE/Alu/PET having a thickness of respectively 80 $\mu$m/9 $\mu$m/12 $\mu$m. Such a film has a permeation of less than 10% product loss/year at 35° C./20%RH, so that the active composition keeps the activity it has been designed for.

In another embodiment shown in FIG. 5a, the outer package element (19) is designed as an integral part of the article (1), which is attached to the other elements, for example the cell system (10) or the absorbent support (12) material. The film material which is used should feature barrier properties to liquid, gas, and vapors, as previously defined for the separate outer package, so as to obtain a permeation of less than 10% product loss/year at 35° C./20%RH. For example, and as shown in FIGS. 5a and 5b, the film (19) is integrated as a back-sheet of the article. Preferably, as shown in FIGS. 5a and 5b, the surface of said barrier backing sheet is greater than the surface of the absorbent pad, so that once folded, the peripheral portions of the backing sheet are sealed to close the article as a packaging unit (see FIG. 5b).

The support material

In a preferred embodiment of the invention, the cell system (10) is coupled to a support material (12). In a first embodiment of this invention, said support material is made out of a liquid impervious material, such as for example a flexible pouch which contains the cell system. In another embodiment of this invention, the support material is a dispersing material (12) for controlling the application of the active composition and is for example, a fibrous pad for facial cleaning, preferably made out of an absorbent material such as cotton, a wipe for body or household cleaning made out of a non-woven material, a pad to be used for wound-protection, as shown for example in FIGS. 1, 2 or 4. Said dispersing material (12) can have any shape, and dimensions suitable for containing or being coupled with a cell system (10) with dimensions as defined above. Once the active composition contained inside the cell (11) has been released, said composition disperses into the structure of the dispersing material, up to its surface. The structure of said dispersing material can be chosen so as to fit the purposes of the article (1): it can have a smooth surface for pampering, or a rough surface for cleaning, rubbing or removing dead skin for example, or it can be spongy for moisturizing/impregnating the surface to treat. The thickness, shape and dimensions of the dispersing material should be chosen relatively to the number of cells (11) comprised inside the cell system (10), and the volume of active composition contained inside each cell (11).

The flow control means

It has been found that in some occasions, and particularly when the active composition contained inside the cells (11) comprises a liquid or cream form, spillage of said composition can occur at the time the cell (11) is ruptured, even when the cell system (10) is coupled to or associated with a dispersing material (12). To prevent spillage and/or ensure good absorption and diffusion of the composition at the surface of the absorbent material (12), if any, the article (1) of the present invention is provided with a means to control the flow of released active composition when the cell (11) bursts.

As shown in FIGS. 3 to 5a, the flow-control means (15) is a film which covers at least the dome (14) side of the cell (11) and comprises at least one restricted area for the active composition to pass through, from the cell (11) to the outside medium. Optionally, said film also covers the bottom (13) of the cell (11), so as to prevent any spillage of the composition from the bottom (13) side of the cell (11) in case of accidental or intentional burst of said bottom (13) of the cell (11). In one embodiment, the flow-control means (15) is provided with a cut-out portion (16), through which the active composition released from the cell (11) is directed. In another embodiment, the flow-control means (15) is achieved by a cut-out portion of the film onto which a flow-control window (17) such as for example a grid material, or a sheet of a porous material is adapted, as shown in FIGS. 4 and 5a. Such a grid material is described for example in U.S. Pat. No. 3,929,135 to Thompson, or in U.S. Pat. No. 4,324,246 to Mullane, or in U.S. Pat. No. 4,342,314 to Radel. Another grid material which can be used is known under the trademark name "DRI-WEAVE™" marketed by The Procter & Gamble Company. The surface of the portion through which the product will be dispensed may be adapted, for example in view of the viscosity of the product, and also in view of the application of this product. Typically, the surface is comprised within the range of 1 to 1500 mm$^2$, preferably 25 to 700 mm$^2$.

Preferably in both of the preceding embodiments, as shown in FIG. 4, the cut-out portion (16) is aligned with the top of the cell's dome (14) and as shown in FIGS. 5a and 5b, the cut-out portion (16) or the flow-control window (17) is not aligned with a cell (11) so that the way of released composition from the cell to the exterior—for example, to the absorbent cotton pad (12)—is diverted. This allows to better prevent spillage of composition to the exterior, especially in case said composition has a very low viscosity (i.e., less than 100 cps measured with a viscosity meter at 20° C., 1200 rpm).

Alternatively, when the cell has the shape of sachet made of a film which is folded in halves, with sealings on the sides, the flow control means (15) can be an extension (24) of the sachet which comprises, for example, a punched portion (16), as shown in FIG. 7. The cell (11) and its extension (24) from a one-piece element. The main sachet-cell (11) which is filled with a product, and its flow-control extension (24) are separated by a peelable seal (23). Both are manufactured from the same film which is folded in two halves and sealed, with one median seal (23), so that when the user applies a pressure on the top of the filled portion of the sachet (11), it breaks the peelable seal (23), creating a channel between the sachet (11) and the flow-control extension (24), and the product is released through the punched portion (16).

EXAMPLES

Different possible embodiments of articles comprising a cell system according to the present invention will now be described in detail, with reference to the accompanying figures.

In a first embodiment of the present invention, as shown in FIGS. 5a and 5b, one article (1) comprises a cell system (10) with one cell filled with an active composition. The cell is made out of a material which is a barrier to liquids, gases, vapors and solvents, as defined previously in the description, which can be for example a laminated film LDPE/Alu/PET having a thickness of respectively 80 µm/9 µm/12 µm. The cell is covered by a flow control means, such as a film with a cut-out portion (16) which is off-centered relatively to the dome (14) of the cell. The flow-control film is attached onto the cell system (10) by sealing or gluing its edges to the cell system's edges. Said cell system (10) is further sandwiched between two layers of an absorbent material (12) such as cotton, so as to create an absorbent cotton pad with an integrated burstable cell where the two outer layers of cotton can be glued or taped one to the other, but are preferably sealed, using the thermoplastic material of the cell system (10) and/or the thermoplastic material of the flow-control means (15) as sealing agent(s). The cotton pad further comprises an integrated outer package. Said outer package (19) is integrated to the article (1) as a backing sheet which is glued or sealed to the outer side of the pad opposite to the dome (14) of the cell, as shown in FIG. 5a. Preferably, the surface of the backing sheet is slightly superior to the surface of the cotton pad, so that when the pad is folded into two halves into a clamshell-like article (see FIG. 2), both halves being maintained in closed position by a peelable peripheral seal (20), the backing sheet protects the whole cotton pad inside from the outside medium. The clamshell article (1) is used by peeling or cutting the outer package open, bursting the cell to release the active composition into the cotton pad, and then using it. Preferably also, the cell is off-centered from the pad's folding, so as to reduce the risk of accidental squeeze in the pad's folding, and burst of the cell during transportation or storage. The clam-shell structure enables the consumer to use a pad whose surface which comes in contact with the surface to treat has never been in contact with another surface (i.e. fingers of the user or neck of a bottle), and thus is very clean, even once the active composition impregnates the pad. This renders this structure particularly useful for cosmetic purposes.

The present embodiment is best achieved by providing the cell with an easy opening means. Said means can be of any type but more preferably of one of the types previously described. For example, it is a laser scoring which is located onto each cell's dome (not shown in the drawings).

Figure 2:
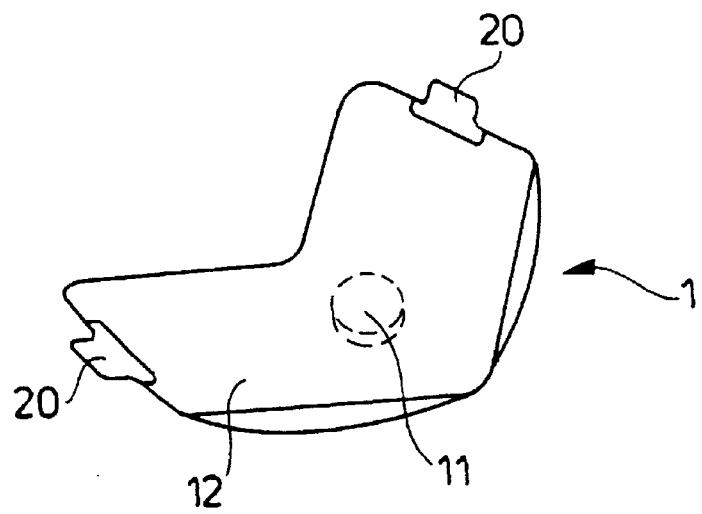
FIG. 2 is a perspective view of an article comprising a cell system and an absorbent support folded in half, the article being shown in partially opened position.

In a second embodiment of this invention, and as shown in FIG. 2, each article (1) comprises a cell system (10) with one cell (11) filled with the active composition. Said at least one cell is covered by a flow control means, such as a film with a cut-out portion (16) which is off-centered relatively to the dome (14) of the cell. The flow-control film is attached onto the cell system (10) by sealing or gluing its edges to the cell system's edges. It further comprises an absorbent cotton pad (12) which contains the cell system (10). The pad is folded into two halves which are maintained by sealing portions (20), which are glued, peel-sealed, taped, or maintained by another suitable means for securing the pad in folded position while being easily openable during use. The barrier to liquids, gases or vapors is achieved by a secondary outer package (not shown) which is for example a pouch made out of a laminate LDPE/Alu/PET having a thickness of respectively 80 µm/9 µm/12 µm. Said secondary barrier package groups one or more article(s).

In a third embodiment of this invention, and as shown in FIG. 1, the article (1) comprises a cell system (10) with several cells (11) filled with a liquid active composition. The cells are made out of a plastic film, for example a LDPE, which has no barrier properties, but which is easy to burst by applying a single finger press thereonto. The cells are covered by a flow control means, such as a film with a cut-out portion (16) which is off-centered relatively to the dome (14) of the cell (not shown). Said cut-out portion is covered by a grid material, such as a plastic mesh (as shown for example in FIG. 5a), for increased control of the flow of liquid contents which is dispensed from the cell once it has been ruptured. The flow-control film is attached onto the cell system (10) by sealing or gluing its edges to the cell system's edges. It further comprises a flat absorbent pad (12), for example a flat cotton pad which contains the cell system (10). The barrier to liquids, gases or vapors is achieved by packing one or more articles inside a secondary package such as a flexible pouch made out of for example a laminate LDPE/Alu/PET having a thickness of respectively 80 µm/9 µm/12 µm.

Contents

The active composition which is contained inside the cell can be of any type, for example a face cleaning lotion or cream, a disinfectant composition, a composition for household cleaning purposes, a perfume composition, a polish, a medicament . . . Its viscosity is preferably comprised within the range of 0.1 to 6000 cps measured at 20° C. In one embodiment of the present invention, the active composition is a liquid face cleaning and disinfecting composition known under the trademark Clearasil™ manufactured and sold by The Procter & Gamble Company. Such a composition typically comprises for example: Purified Water; Alcohol 96%; Diethyl Phthalate; Myrtrimonium Bromide; Ceteareth-14; Disodium Cocoamphodiacetate 38%; Tartaric Acid; Allantoin; Chlorhexidine Digluconate 20%; Perfume Balance PSV 1270; Cl 42051 Acid Blue 3 E131. Detailed examples of such composition are disclosed for example in European Patent Applications EP-A-0614353 and EP-A-0614354 to the Procter & Gamble Company.

What is claimed is:

1. A cell system (10) with at least one burstable cell (11) filled with an active composition, the cell system being characterized in that it comprises a means (15) to control the flow and direction of the cell's contents, once said at least one cell has been ruptured.

2. A cell system according to claim 1, wherein the cell has a dome and the means (15) for controlling the flow and direction of the cell's contents, is positioned outside and all around the cell's dome and is provided with a window (17) of a predetermined dimension through which the cell's contents is released to the outside.

3. A cell system according to claim 2, wherein the window (17) is made out of a grid material.

4. A cell system according to claim 2, wherein the window (17) is aligned with the top of the cell's dome.

5. A cell system according to claim 1, wherein the means (15) for controlling the flow and direction of the cell's contents is an extension (24) of the cell which is punched with a cut-out portion (16), the cell and its extension (24) forming a one-piece element, and being separated by a peelable median seal (23).

6. A cell system according to claim 1, wherein the cut-out portion (16) is comprised within the range of 1 to 1500 mm$^2$.

7. A cell system according to claim 1, wherein said at least one cell (11) has an internal volume which is comprised within the range of 0.01 ml to 5.0 ml.

8. An article comprising a cell system as claimed in claim 7.

9. An article according to claim 8, wherein the cell system is coupled to a support material in the form of a dispersing material and said dispersing material (12) is a fibrous pad.

10. A cell system according to claim 1, wherein 50 to 99% of the cell's volume is filled with the composition.

11. A cell system according to claim 10, wherein said cell system is coupled to a dispersing article (12) for controlling the application of said active composition, once said at least one cell has been burst.

12. A cell system according to claim 11, which comprises a backing sheet (19), said cell system and backing sheet being folded in half and the two halves being attached together by a peripheral openable seal (20), so as to create a clamshell-like article.

* * * * *